(12) United States Patent
Lowe et al.

(10) Patent No.: US 6,458,377 B1
(45) Date of Patent: Oct. 1, 2002

(54) WETTABLE POWDER COMPOSITIONS OF IONOPHORE ANTIBIOTICS

(75) Inventors: Lionel B. Lowe, Dural (AU); Derek G. Moore, Auckland (NZ)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/982,746

(22) Filed: Oct. 18, 2001

Related U.S. Application Data (62) Division of application No. 09/068,221, filed as application No. PCT/NZ96/00117 on Oct. 18, 1996, now Pat. No. 6,365,174.

(30) Foreign Application Priority Data

Nov. 2, 1995 (NZ) ................................. 280384

(51) Int. Cl.$^7$ ............................. A23K 1/18; A61K 31/35
(52) U.S. Cl. ........................ 424/438; 424/405; 424/409; 424/410; 424/442; 514/460
(58) Field of Search ................................. 424/405, 406, 424/438, 442, 421, 409, 489, 499, 410; 514/460

(56) References Cited

U.S. PATENT DOCUMENTS

| | | | |
|---|---|---|---|
| 5,112,604 A | | 5/1992 | Beaurline et al. |
| 5,300,439 A | | 4/1994 | Charlton |
| 5,624,710 A | * | 4/1997 | Grabitz .................. 427/212 |
| 5,874,103 A | | 2/1999 | Moore et al. |
| 5,985,891 A | | 11/1999 | Rowe |

FOREIGN PATENT DOCUMENTS

| | | |
|---|---|---|
| EP | 0024189 | 2/1981 |
| EP | 0139595 | 5/1985 |
| EP | 0150596 | 8/1985 |
| EP | 0405930 | 1/1991 |
| EP | 0470667 | 2/1992 |
| EP | 0556057 | 8/1993 |
| EP | 0620001 | 10/1994 |
| EP | 0671174 | 9/1995 |
| WO | WO 95/17091 | 6/1995 |

OTHER PUBLICATIONS

E.F. Reynolds (ed.) "Martindale, the Extra Pharmacopoeia," $28^{th}$ edition, (1982), p. 954, $3^{rd}$ col; p. 960; $2^{nd}$ col; pp. 1068–1069 and p. 1442, $2^{nd}$–$3^{rd}$ column.

A.R. Gennaro (ed.) "Remington's Pharmaceutical Sciences," $17^{th}$ ed (1985), pp. 774–775; pp. 814–815; pp. 1299–1300 and p. 1317, $1^{st}$ column.

Freyer, et al., "Use of Xantham Gum to Suspend Large Particles During Flow Cytometric Analysis and Sorting," Cytometry 10: 803–806 (1989).

* cited by examiner

Primary Examiner—Neil S. Levy
(74) Attorney, Agent, or Firm—John C. Demeter (57) ABSTRACT

A dry composition of an ionophore antibiotic such as monensin comprising from 10 to 95% (when expressed as the sodium salt) of at least one crystalline ionophore antibiotic, from 0 to 10% antifoam agent(s), from 0.1 to 20% wetting and/or surfactant agent(s), from 0.1 to 10% dispersal agent(s), and from 0.1 to 20% suspension agent(s).

The use of the composition is as a suspension in water alone or in conjunction with a milk replacer composition and/or a milk extender composition in water as a calf feed composition.

3 Claims, 6 Drawing Sheets

WETTABLE POWDER COMPOSITIONS OF IONOPHORE ANTIBIOTICS

This application is a division of Ser. No. 09/068,221 filed Dec. 18, 1998 U.S. Pat. No. 6,365,174 which is a national stage of PCT/NZ96/00117 filed Oct. 18, 1996.

TECHNICAL FIELD

The present invention relates to wettable powder compositions of an ionophore antibiotic useful as a feed supplement to a ruminant animal (including a suckling ruminant juvenile animal), methods of using such a composition in conjunction with milk and/or milk replacement powders and as a milk replacer for such ruminant animals and related means and methods.

BACKGROUND ART

In U.S. Pat. No. 3,839,557 of Eli Lilly and Company (the fill content of which is hereby here incorporated by reference) there is disclosure of a method of increasing the efficiency of feed utilisation by ruminant animals having a developed rumen function where an antibiotic chosen from the group A204 (U.S. Pat. No. 3,705,238) dianemycin (fermentation product of *Streptomyces Hygroscopicus* NRRL 3444) monensin (U.S. Pat. No. 501,358), X537A (Netherlands patent 70.12,108) nigericin (U.S. Pat. No. 3,555,150) and X206 (1951, Berger et al, *J. Am Chem. Soc.* 73, 5295–98 (1951)), and certain derivatives thereof are orally administered to the ruminant animals whose fed efficiency is to be increased.

Examples of appropriate ruminant animals given are cattle, sheep and goats.

The invention of U.S. Pat. No. 3,839,557 is indicated as being useful to ruminants which have a developed rumen function. Young ruminants (basically those still unweaned) are stated as functioning as monogastic animals and that it is not until such young ruminant eat solid feed contain cellulose, starch and other carbohydrates that the function of the rumen begins to develop and the microbiological population of the rumen increases.

Dosages given in U.S. Pat. No. 3,839,557 (in general propionate-increasing amounts) are in the range of from about 0.05 mg of antibiotic per kg of body weight per day to about 2.5 mg/kg/day.

Administration methods given in U.S. Pat. No. 3,839,557 suggest incorporation of the antibiotic compound or compounds into tablets, drenches, boluses or capsules. Them is disclosure that drenches of such antibiotics can be prepared most easily by choosing a water soluble form of the antibiotic but that if an insoluble form is desired for some reason a suspension can be made. There is an indication that suspensions of insoluble forms of the antibiotics can be prepared in non solvents such as water but that suitable physiologically-acceptable adjuvants are necessary in order to keep the antibiotics suspended The adjuvants can be chosen from amongst thickeners, surfactants, hydrophilicity agents, density affecting agents and surface tension affecting agents.

U.S. Pat. No. 3,839,557 suggests that a suspendible antibiotic may be offered as a dry mixture of the antibiotic in adjuvants to be diluted before use. A suggestion is made that such antibiotic can be incorporated into drinking water by adding a water soluble or water suspendible form of the desired antibiotic to the water in a proper amount. There is also disclosure that the method of administration of the antibiotic can be practised in combination with other treatments, i.e. with other drugs used in combination.

European Patent Application 0139595 of Koffolk (1943) Limited relates to liquid feeds and milk replacers for ruminants and particularly for suckling ruminants. Such compositions that are disclosed contain ionophore antibiotics such as monensin, narasin, lasalocid (U.S. Pat. No. 3,715,372) and solinomycin.

In one form of the invention of EP 0139595 there is disclosed a liquid ionophore antibiotic composition for ruminants comprising an ionophore antibiotic and at least one non toxic water miscible organic solvent. The invention is also stated as providing a dry water soluble ionophore antibiotic composition suitable for combination with an aqueous medium to form a liquid composition for ruminants, the composition comprising an ionophore antibiotic, a non toxic water miscible organic solvent and a dry water soluble carrier therefor. The invention relates also to process for preparing liquid feeds which involves dissolving such an ionophore antibiotic in a non toxic water soluble organic solvent and admixing the resulting solution with a liquid feed, a water soluble vitamin concentrate or with drinking water.

The preferred ionophore antibiotics are those that have been subjected to an extraction process whereby the antibiotic is no longer in the mycelial form, i.e. is in a crystallisable form or a crystalline form.

Such compositions of EP 0139595 are stated as being liquid milk replacers, or at least being capable of being incorporated in liquid feeds or drinking water for administration to a suckling ruminant.

Example 13 of EP 0139595 refers to spraying in a horizontal mixer of a monensin solution (of the invention of EP 0139595 as defined) on a dry milk replacer and then the subsequent "dissolving" thereof with water.

DISCLOSURE OF INVENTION

The present invention relates to an alternative milk replacer or milk extender composition to any of those disclosed and to related methods.

In a first aspect the present invention consists in a dry composition of an ionophore antibiotic capable of being suspended in water directly to form a suspension (with or without any other addition(s)) deliverable into a ruminant (particularly a suckling ruminant) or, capable upon admixture with a dry milk powder and/or milk substitute powder, of in turn then being mixed with water to form (with or without any other addition(s)) a suspension deliverable into a ruminant (particularly a suckling ruminant) as a milk replacement or extender, said composition comprising, when expressed weight for weight with respect to the overall dry composition, from 10 to 95% (when expressed as the sodium salt) of at least one crystalline ionophore antibiotic, from 0 to 10% antifoam agent(s), from 0.1 to 20% wetting and/or surfactant agent(s), from 0.1 to 10% dispersal agent(s), and from 0.1 to 20% suspension agent(s).

As used herein percentages of ionophore antibiotic refer to the antibiotic in any suitable form (eg. acid or salt) but expressed for the purpose of the ranges by reference to its weight as the sodium salt as against the overall weight to the dry composition (where for the purpose of the overall weight the antibiotic is also accounted for by reference to its weight as the sodium salt).

Preferably said antibiotic is from 90 to 95% w/w
Preferably said antifoam agents is from 0 to 2% w/w
Preferably said wetting surfactant agents is from 0.1 to 5% w/w.
Preferably said dispersal agent is from 0.1 to 5% w/w
Preferably said suspension agent is from 0.1 to 5% w/w.
A preferred composition has
from 10 to 95% (eg. 10 to 80%) of at least one crystalline ionophore antibiotic,
from 0.1 to 0.5% antifoam agent(s),
from 0.1 to 0.5% wetting and/or surfactant agent(s),
from 0.1 to 0.5% dispersal agent(s), and
from 0.1 to 0.5% suspension agent Preferably said ionophore antibiotic is selected from group consisting of Monensin, Lonomycin, Ionomycin, Laidlomycin, Nigericin, Grisorixin, Dianemycin, Lenoremycin, Salinomycin, Narasin, Antibiotic X206, Alborixin, Septamycin, Antibiotic A204, Maduramicin and Semduramicin, Compound 47224, Lasalocid (also including factors A, B, C, D and E), Mutalomycin, Isolasalocid A, Lysocellin, Tetronasin, Echeromycin, Antibiotic X-14766A, Antibiotic A23187, Antibiotic A32887, Compound 51532 and K41.

Preferably said ionophore antibiotic is Monensin.
Preferably said Monensin is Sodium Monensin.
Preferably said antifoaming agent is selected from the group consisting of Silicone antifoam powder such as Wacker ASP 3 hereinafter referred to.

Preferably said wetting agent is selected from the group consisting of Sodium lauryl sulfate (anionic sulfates) such as CARSONOL™ SLS-R (LONZA) or EMAL™ (POLEKAO).

Preferably said dispersal agent is selected from the group consisting of colloidal anhydrous silica such as Aerosil 200 Chemische Fabrik Kirsh Gmbtt.

Preferably said suspension agent(s) is or are selected from the group consisting of refined food grade galactomannan such as guar gum.

In a further aspect the present invention consists in the use of a dry composition in accordance with the present invention after admixture with water to form a suspension as a feed supplement of a suckling or other ruminant.

Preferably said use involves milk powder or a milk substitute which is mixed into water either subsequently to, simultaneously with or prior to the suspension of the composition of the present invention in such water.

The present invention also consists in, as a dry composition, a dry composition in accordance with the present invention and a milk powder and/or milk replacement powder.

In yet a further aspect the invention consists in a calf feed composition comprising a substantially homogeneous aqueous suspension of, with respect to the composition volume,
(i) from 2 to 16 mg/L of a dry composition in accordance with the present invention,
(ii) optionally, a milk replacer composition, and
(iii) optionally, a milk extender composition.

Preferably from 5 to 30 g/L of a dry milk replacer composition has been included.
Preferably 10 to 25 g/L, eg. 15, or 20 g/L.
Preferably from 1 to 3 g/L milk extender (preferably about 2 g/L) is present or, preferably, is present in addition to a or the dry milk replacer composition.

In yet a further aspect the invention consists in a dry composition of monensin capable of being suspended in water directly to form a suspension (with or without any other addition(s)) deliverable into a ruminant or, capable upon admixture with a dry milk powder and/or milk substitute powder, of in turn then being mixed with water to form (with or without any other addition(s)) a suspension deliverable into a ruminant as a milk replacement or extender, said composition comprising, when expressed weight for weight with respect to the overall dry composition,
95% (when expressed as the sodium salt), of crystalline sodium monensin,
19% silicone antifoam powder,
3.5% sodium lauryl sulfate,
2.5% colloidal anhydrous silica, and
1.5% Guar gum In a still further aspect the invention consists in a calf feed composition comprising a substantially homogeneous aqueous suspension of, with respect to the composition volume,
(I) from 2 to 16 mg/L of a composition comprising
95% (when expressed as the sodium salt) of crystalline sodium monensin,
19% silicone antifoam powder,
3.5% sodium lauryl sulfate,
2.5% colloidal anhydrous silica, and
1.5% Guar gum, AND
(II) 15 to 20 g/L of a milk replacer composition, and/or 1 to 3 g/L of a milk extender composition.

In still a further aspect the invention consists in, as a premix. The components (i) and (ii), (i) and (iii) or (i), (ii) and (iii) for a calf feed composition as defined hereinbefore.

In still a further aspect the present invention consists in a method of increasing feed conversion and growth rate of suckling ruminants which involves the administration orally or self administration orally of a composition of the present invention in conjunction with at least water into such ruminants.

Coccidiosis is a serious and common disease of dairy calves. During much of the time that dairy calves are at risk of coccidiosis, some or all or their diet comprises milk, milk replacers or milk extenders. The intake of these milk components is more consistent and controllable than other components of the diet. For this reason it is desirable to be able to administer anti-coccidial agents to these animals in the milk portion of their diet.

Monensin sodium in prior art formulations does not remain evenly distributed in milk, milk replacers or milk extenders for a sufficient period time to make it practical or safe for use in this manner.

A "milk extender" contains vitamins and minerals but in itself is not a "milk replacer".

Milk replacers are, as the name suggests, compositions capable of replacing the natural milk of the species. Typically a milk replacer is made up from a skim milk powder (usually of the same species of mammal) plus a source of fat which can either be of animal or plant origin. In the case of cattle this fat replaces the normal cream in whole cows milk.

The present invention therefore envisages a calf feed to supplement or replace the natural milk feed of an animal. The calf feed may comprise
i) a milk replacer having an anti coccidial agent provided in accordance with the present invention, substantially evenly distributed there throughout
ii) a milk replacer and milk extender mixed/blended composition itself including an anti coccidial agent (whether blended with the milk replacer, the milk extender or both simultaneously).

Calves receive and ingest milk replacers and extenders within 24 hours of preparation.

Monensin was selected as the ionophore antibiotic for detailed trialing.

To ensure the safety of monensin wettable powder as a delivery vector for ingestion as a liquid it was considered necessary that monensin, delivered as part of a calf feed eg. An aqueous composite as a milk replacer and/or milk extender, should remain evenly distributed for 24 hours after homogeneous mixing with water.

The purpose of these trials was to determine the distribution characteristics of monensin wettable powder in aqueous preparations of milk replacers and milk extenders.

A preferred form of monensin wettable powder of the present invention having the formula as follows was used in the following trials and assays.

Monensin (Sodium) Wettable Powder

A preferred dry composition of an ionophore antibiotic (this includes a mixture of different types) comprises 10 to 95% of at least one crystalline ionophore antibiotic (the percentage being when the antibiotic is expressed as its sodium salt (eg. Monensin sodium whether or not it is in fact a monensin salt or indeed a sodium salt), 0 to 2% antifoam agent(s), 0.1 to 5% wetting and/or surfactant agent(s), 0.1 to 5% dispersal agent(s), and 0.1 to 5% suspension agent.

BRIEF DESCRIPTION OF DRAWINGS

A most preferred formulation and that trialed as described hereinafter by reference to FIGS. 1 to 11 was prepared as now follows:

| | | |
|---|---|---|
| RUMENSIN ™ Technical (Monensin sodium) | Elanco Animal Health division of Eli Lilly Australia Pty Ltd, 112 Wharf Road, NSW 2114, Australia EL5167 (929 gai/Kg) | 915 g |
| Silicone Antifoam Powder ASP3 | Wacker Silicone available from Amcor Trading, PO Box 33 Drumoyne NSW 2047 Australia | 10 g |
| EMAL ™ 10 NEEDLE sodium lauryl sulfate | PT Polekao Indonesia Chemicals available in Australia from P & M O'Brien Trading Pty Ltd, ACN 054787161 (Lot No.1410) | 35 g |
| AEROSIL 200 ™ (colloidal anhydrous silica) | Chemische Fabrik Kirsh GmbH Product Code HH01 availabic in Australia from Chemical Distributors Fax 61 2 9385867 | 25 g |
| Guar gum WW 250 F (galactomannan E412) | Woods or Woods Pty Ltd ACN 001 092 066 Australia | 15 |
| | | 1000 g |

Monensin sodium wettable powder was formulated this to enable monensin to remain evenly distributed in aqueous calf feed compositions for a period of 24 hours.

Calf Feed Components of Trials

| | |
|---|---|
| Milk Replacer | VEANAVITE ™ Instant Calf Milk replacer 13426 available from Philip Grant, PO Box 160, Cowra, NSW 2794, Australia. |

-continued

| | |
|---|---|
| Milk Extenders | PREMAX ™ Calf Booster [available from Ridley Agriproucts Pty Ltd 39 Oxford Street, Epping, NSW 2121, Australia.] CALFGO ™ (Rhone Poulenc) B/N 55654 [available from Rhone Poulenc Animal Nutrition 19-25 Paramount Road, West Footscray, Victoria 3012, Australia.] |
| Monensin (sodium) | MONENSIN (sodium) (RUMENSIN ™) WETTABLE POWDER (B/N 470 Assay No. 950103 (86.7%)) of the present invention ie. The blend resulting from the immediately preceding formulation. |
| Water | — |

Cow's Milk Standard

The wettable powder of the present invention was developed for use in milk replacers which may additionally include milk extenders. It is the suspendability of the wettable powder in such aqueous compositions of milk replacers additionally enhanced where desired by milk extenders, that is of importance. For this reason therefore the suspendability of monensin wettable powder in water was not considered a useful standard as both milk and milk replacer based aqueous compositions are much more complex liquids than mere water particularly in regard to the fat, sugar, and protein present. It was therefore considered that for the purpose of assaying for the strengths of monensin during the trials an appropriate standard for comparative purposes (the assay for monensin) was a known strength composition of monensin sodium in whole cows milk.

First a known strength (8000 mg/L) crystalline monensin sodium solution in methanol was prepared. This was then used to formulate the assay standard formulations (the methanol having been evaporated by a stream of nitrogen) after pipetting of amounts of the monensin/methanol into 2 liter volumetric flasks as follows:

| Monensin concentration in milk(mg/L)(as expressed as Monensin and not the salt) | (mL) of the monensin/methanol solution | Whole Cows Milk (L) |
|---|---|---|
| 2 | 0.5 | 2 |
| 6 | 1.5 | 2 |
| 8 | 2.0 | 2 |
| 12 | 3.0 | 2 |
| 16 | 4.0 | 2 |

The monensin in milk concentrations were achieved by the addition of cow's milk into the volumetric flask In Milk Replacers with Milk Extenders It is anticipated that for commercial use monensin wettable powder will be added to aqueous calf feed compositions (milk replacers optionally with milk extenders) at a rate of 6 mg/L monensin. The addition rates of monensin used in this trial were chosen to represent a range around this anticipated use rate (i.e. 2, 6, 8, 12, 16 mg/L).

For the purpose of the trials the milk replacer used was VEANAVITE™ instant calf milk replacer identified above.

Two formulations of milk extender (Formulations I and II) were examined in this trial. Both formulations are of commercial milk extenders currently used in Australian market.

| [PREMAX ™ Calf Booster] Milk Extender Formulation I | |
| --- | --- |
| | Per kg |
| Retinyl acetate (vitamin A) | 186,000 IU |
| Cholecalciferon (vitamin D$_3$) | 18,000 IU |
| di-alpha-tocopheryl acetate (vitamin E) | 1.86 g |
| Thiamine hydrochloride | 400 mg |
| Pyridoxine hydrochloride | 150 mg |
| Cyanocobalamin | 20 mg |
| Biotin | 3.0 mg |
| Folic acid | 8.0 mg |
| Menadione | 65.0 mg |
| Nicotinic acid | 696.0 mg |
| D-calcium pantothenate | 262.0 mg |
| Choline | 67.86 mg |
| Selenium (Se) | 1.0 mg |
| Cobalt (Co) | 3.0 mg |
| Iodine (I) | 15.0 mg |
| Copper (Cu) | 292.0 mg |
| Manganese (Mn) | 749.0 mg |
| Zinc (Zn) | 900.0 mg |
| Ferrous iron (Fe++) | 1.13 g |
| Lysine | 2.00 g |
| di-Methionine | 2.00 g |
| Magnesium (Mg) | 469.97 g |
| Maximum fluorine (F) | Nil |
| Carrier Prebase ™ | ? |

| [CALGRO ™] Milk Extender Formulation II | |
| --- | --- |
| | Per kg |
| Vitamin A | 40,000 IU |
| Vitamin D | 6,000 |
| Vitamin E | 80 mg |
| Vitamin K | 2 mg |
| Thiamine (B1) | 6 mg |
| Riboflavin (B2) | 7 mg |
| Pyridoine (B6) | 4 mg |
| Niacin | 20 mg |
| B12 | 0.05 mg |
| Biotin | 1 mg |
| Vitamin C | 100 mg |
| Pantothenic acid | 13 mg |
| Folic acid | 0.006 mg |
| Choline Chloride | 200 mg |
| Magnesium | 300 mg |
| Copper | 10 mg |
| Cobalt | 0.8 mg |
| Zinc | 70 mg |
| Iron | 150 mg |
| Iodine | 0.8 mg |
| Selenium | 0.2 mg |
| Manganese | 50 mg |
| Molybdenum | 4 mg |
| Avoparcin | 40 mg |

Calf feed formulations trialled were prepared with water with 15 g/L and 20 g/L VEANAVITE™ Instant Milk replacer and either 2 g/L Premax Calf Booster or 2 g/L Calfgro.

15 g/L milk replacer/2 g/L extender formulations were studied at Monensin sodium concentrations of 2 mg/L, 6 mg/L, 8 mg/L, 12 mg/L and 16 mg/L.

20 g/L milk replacers/2 g/L extender formulations were studied at a Monensin sodium concentration of 6 mg/L.

Each monensin wettable powder spiked formulation was sampled at the top and bottom of the prepared volume at 0, 1, 3, 5 and 24 hours. Sample extraction was performed immediately and extracts analysed the same day.

Analyses (i). Pipette two 40 mL portions for zero time analysis.

(ii). At subsequent time points pipette a 40 mL portion from 2.5 cm under the surface (top sample) and 1.5 cm above the container bottom (bottom sample).

(iii). Prepare extracts for HPLC analysis on each 40 mL portion as they are sampled.

(iv). Analysis by HPLC. Monensin is extracted from various milk formulations with dichloromethane and is quantified using a high performance liquid chromatograph (LC) equipped with a post column reactor. Monensin is acid—reacted with vanillin, and the resulting products are measured by a variable wavelength visible detector operating at 520 nm. The method is based on the Lilly Research Laboratories method AM-AA-CR-R150-AB-791.

Milk replacer was prepared at 15 and 20 g/L concentrations since the concentration of milk replacer received by calves is usually varied with the age of the calf.

Results

TABLE 1

Suspension in water of monensin wettable powder with 15 g/L milk replacer and 2 g/L milk extender samples

| Theoretical mg monensin | | mg monensin | | | | |
| --- | --- | --- | --- | --- | --- | --- |
| | Position | 0 Hr | 1 Hr | 3 Hr | 5 Hr | 24 Hr |
| 2 mg/L | | | | | | |
| Extender 1 | Top | 1.9 | 1.9 | 1.8 | 1.9 | 2.0 |
| | Bottom | — | 1.9 | 1.8 | 1.8 | 2.1 |
| Extender 2 | Top | 1.9 | 1.8 | 1.8 | 1.8 | 2.0 |
| | Bottom | — | 1.8 | 1.9 | 1.8 | 2.0 |
| 6 mg/L | | | | | | |
| Extender 1 | Top | 6.0 | 5.9 | 6.0 | 5.2 | 5.7 |
| | Bottom | — | 6.0 | 5.7 | 5.8 | 5.8 |
| Extender 2 | Top | 6.3 | 6.2 | 6.1 | 6.1 | 6.1 |
| | Bottom | — | 5.8 | 5.7 | 5.7 | 6.1 |
| 8 mg/L | | | | | | |
| Extender 1 | Top | 8.0 | 7.4 | 6.9 | 7.2 | 7.4 |
| | Bottom | — | 7.3 | 7.0 | 7.0 | 7.2 |
| Extender 2 | Top | 8.0 | 8.1 | 8.4 | 8.0 | 7.6 |
| | Bottom | — | 7.7 | 7.7 | 7.6 | 7.9 |
| 12 mg/L | | | | | | |
| Extender 1 | Top | 12.5 | 12.2 | 12.3 | 12.5 | 11.9 |
| | Bottom | — | 12.0 | 12.1 | 12.0 | 13.0 |
| Extender 2 | Top | 12.4 | 11.9 | 11.3 | 11.7 | 11.3 |
| | Bottom | — | 12.0 | 11.6 | 11.5 | 11.8 |
| 16 mg/L | | | | | | |
| Extender 1 | Top | 16.6 | 16.7 | 16.4 | 16.0 | 17.1 |
| | Bottom | — | 16.3 | 16.5 | 16.0 | 16.2 |
| Extender 2 | Top | 16.7 | 16.2 | 16.1 | 16.0 | 15.6 |
| | Bottom | — | 16.2 | 16.1 | 15.6 | 15.8 |

TABLE 2

Suspension in water of Monensin wettable powder with 20 g/L milk replacer and 2 g/L milk extender

| Spike | Position | 0 Hr | 1 Hr | 3 Hr | 5 Hr | 24 Hr |
| --- | --- | --- | --- | --- | --- | --- |
| 6 mg/L | | | | | | |
| Extender 1 | Top | 6.0 | 5.9 | 5.8 | 5.7 | 5.9 |
| | Bottom | — | 5.6 | 5.6 | 5.5 | 5.5 |

TABLE 2-continued

Suspension in water of Monensin wettable powder with 20 g/L milk replacer and 2 g/L milk extender

| Spike | Position | 0 Hr | 1 Hr | 3 Hr | 5 Hr | 24 Hr |
|---|---|---|---|---|---|---|
| Extender 2 | Top | 6.0 | 5.6 | 5.6 | 5.7 | 5.6 |
|  | Bottom | — | 5.7 | 5.6 | 5.5 | 5.4 |

Monensin wettable powder remained evenly distributed in the 15 g/L milk replacer solution at all concentrations of monensin for 24 hours after preparation. Please see FIGS. 1 to 10.

Figure 1:
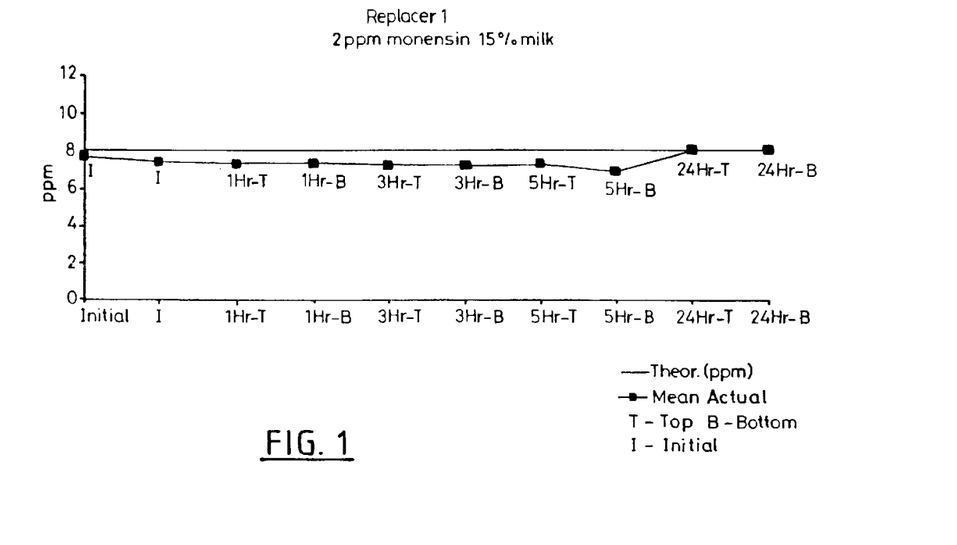
Figure 2:
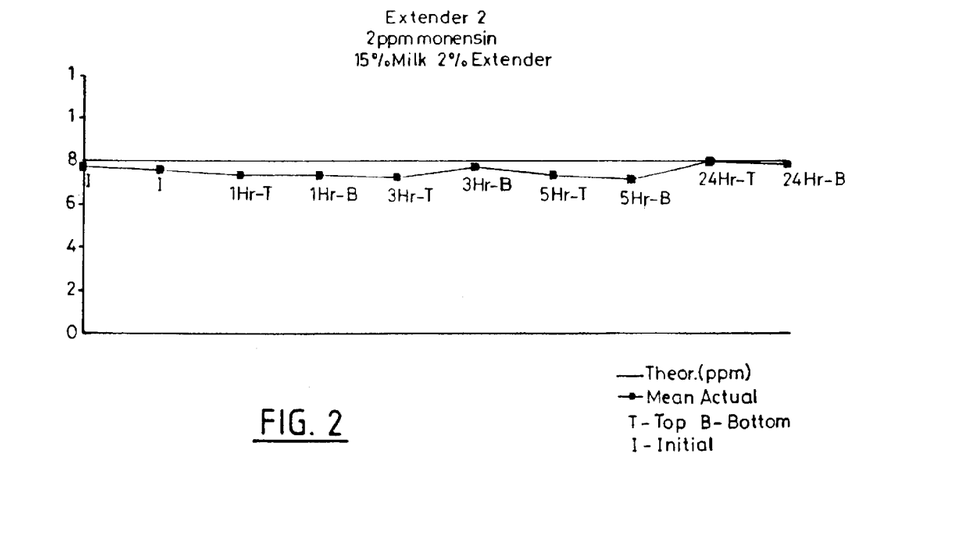
Figure 3:
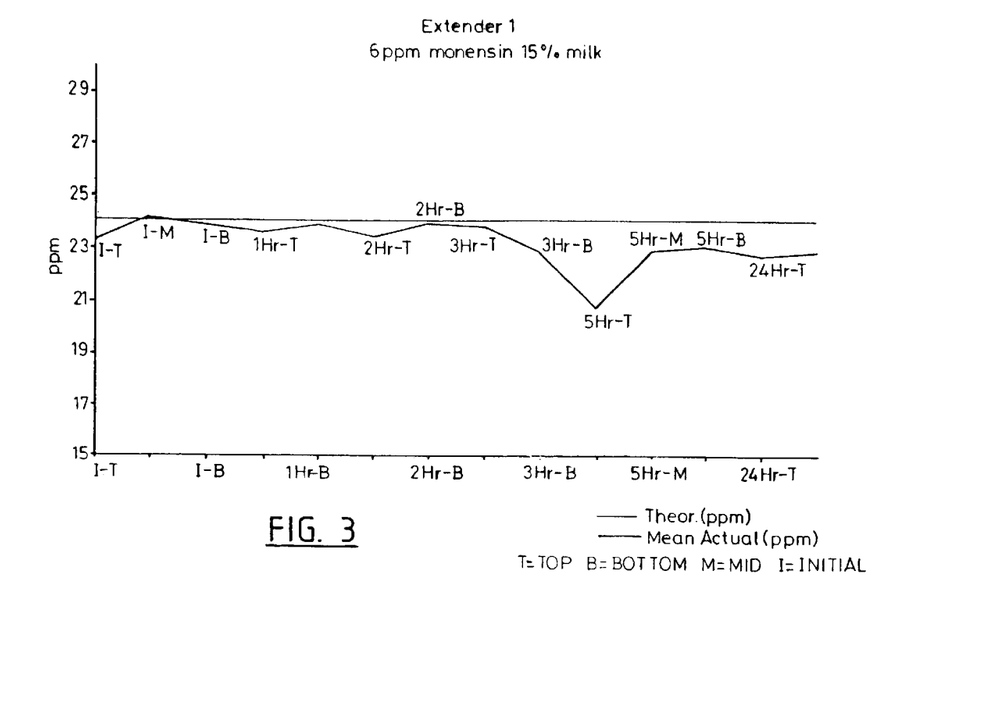
Figure 4:
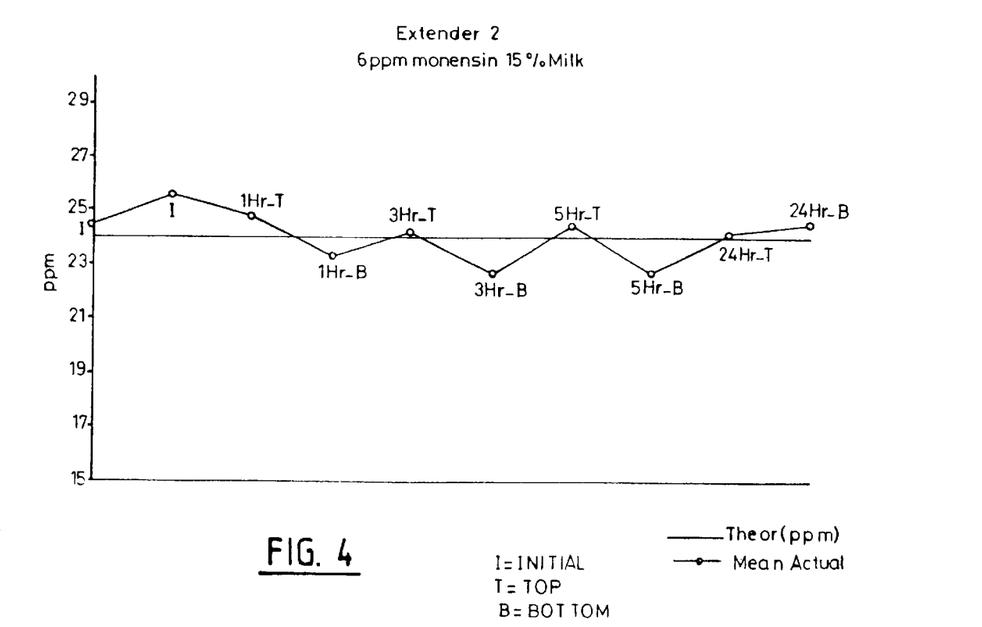
Figure 5:
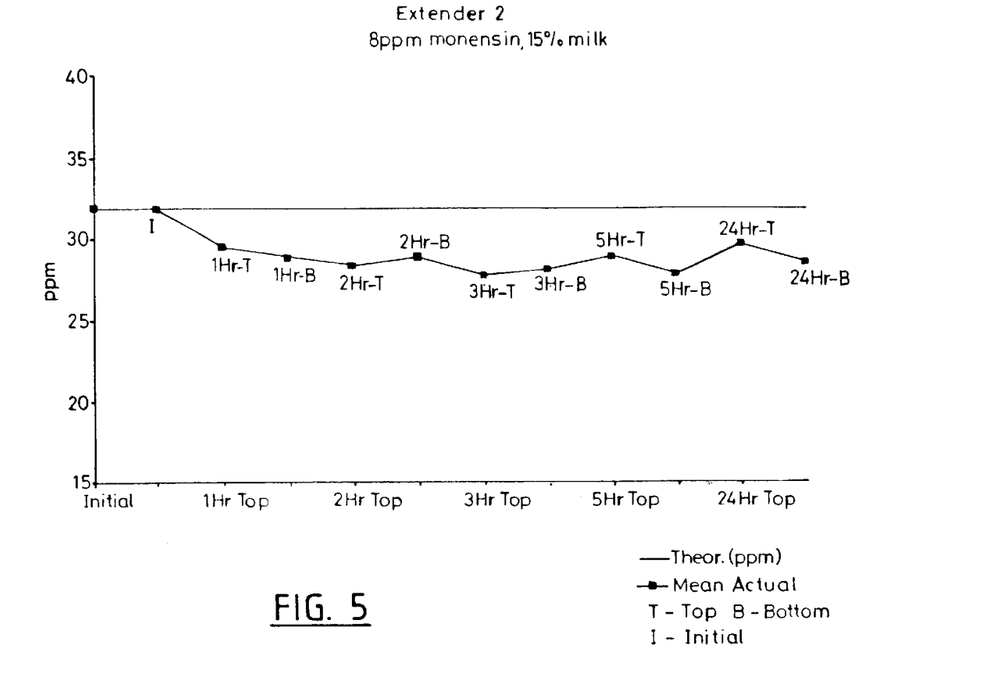
Figure 6:
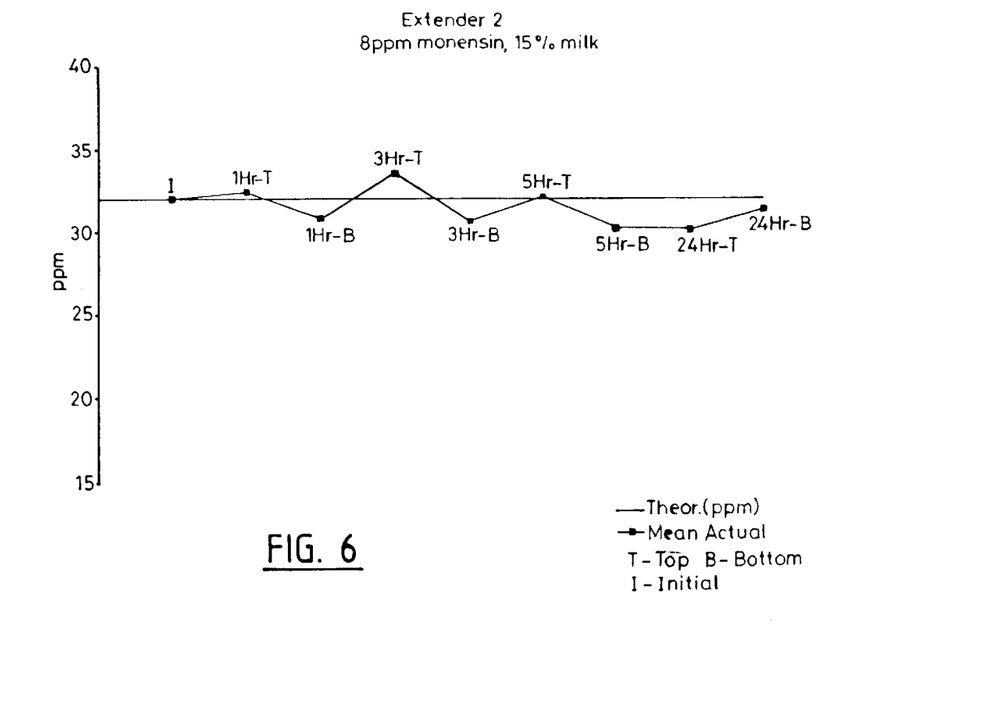
Figure 7:
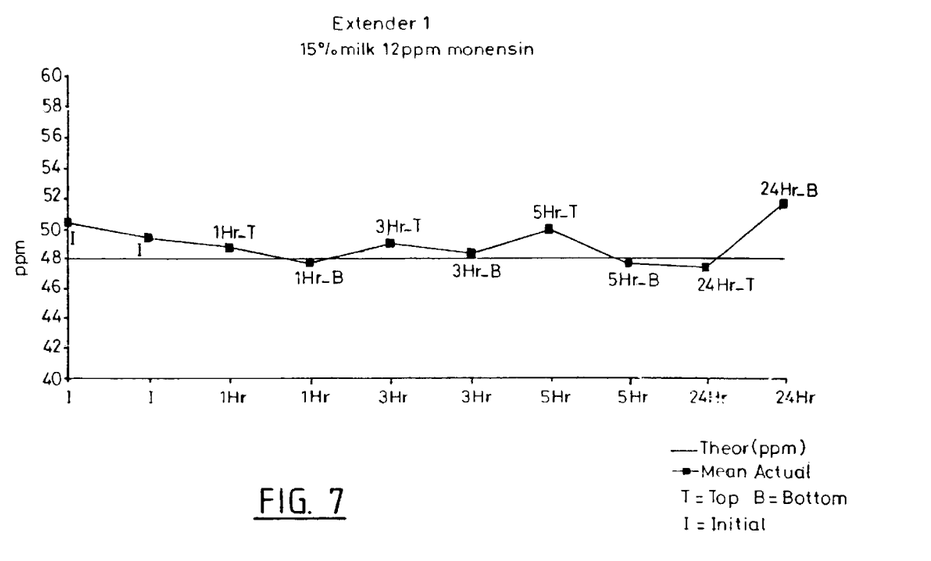
Figure 8:
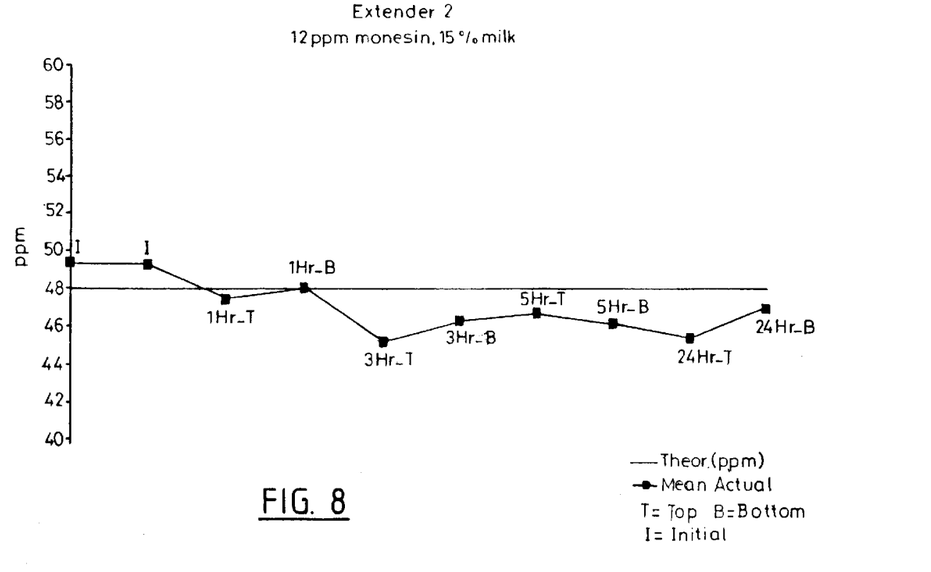
Figure 9:
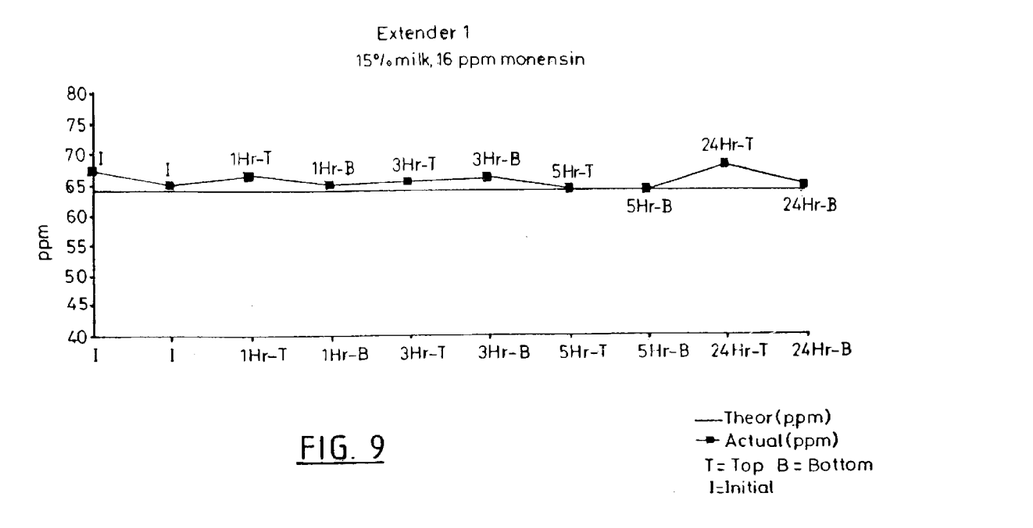
Figure 10:
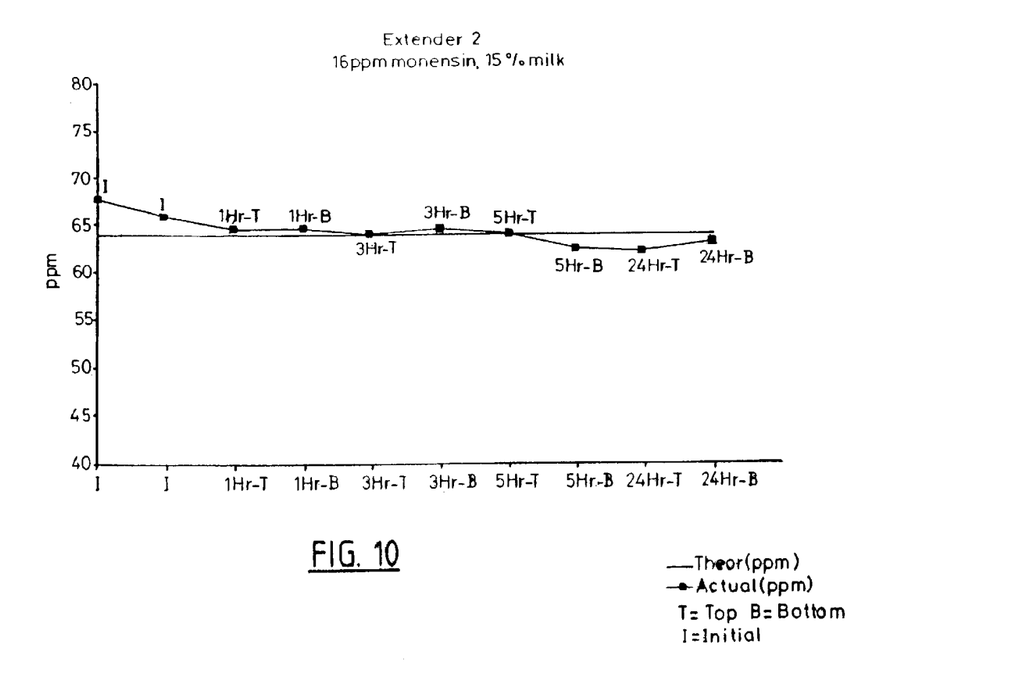
Figure 11A:
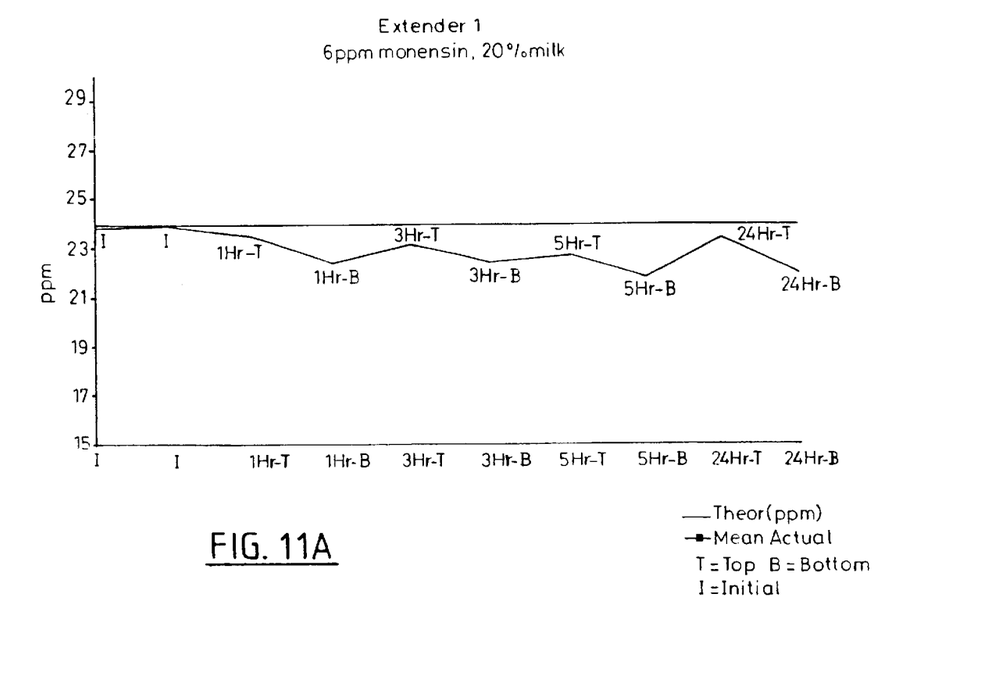
Figure 11B:
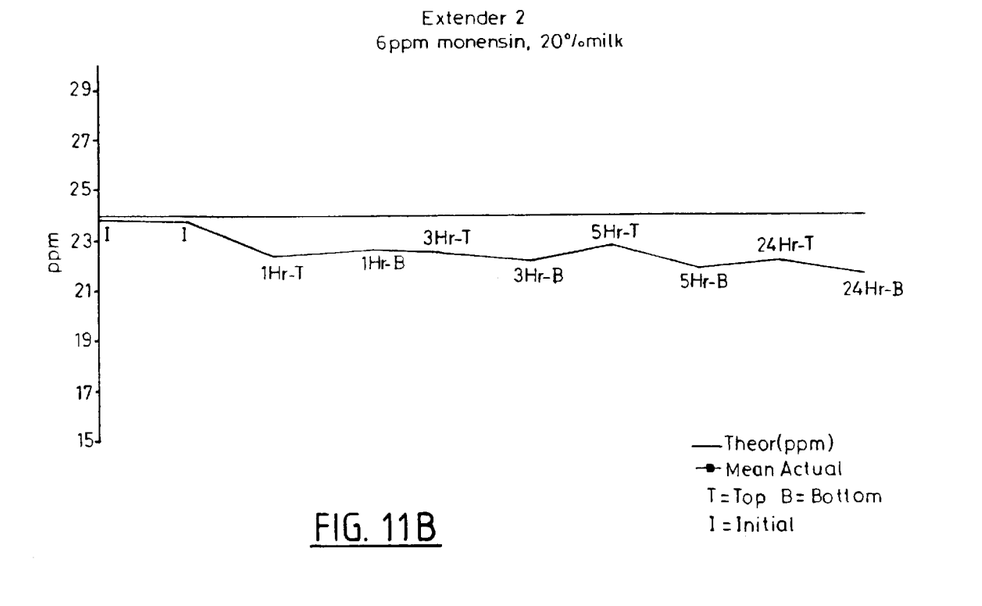

Monensin wettable powder remained evenly distributed in the 20 g/L milk replacer at 6 mg/L for 24 hours after preparation. Please see FIGS. 10, 11A and 11B.

Mixing and Application

A quantity of dry components whether mixed in together simultaneously or in any sequence is capable of easy blending in a cube blender requiring only about 10 minutes low speed blending. Mixture is then passed through a hammer mill to form a powder.

Such a powder can then be blended with a dry milk powder or milk replacement powder and subsequently as required then be suspended along with the milk powder or milk replacement powder in water for delivery into the animal.

Alternatively the composition can be directly suspended into water and if desired sprayed onto milk powder and then either immediately or subsequently that milk powder (or milk replacement powder or a mixture of both) can as required then be made up with additional water to provide the feed supplement for the animal including the ionophore antibiotic delivered by a composition of the present invention.

Other methods of administration include separate suspension of the composition of the present invention in water and the suspension of milk powder or a milk powder substitute in water and then the bringing of the two suspensions together prior to delivery into the animal. They can if desired be serially administered to the animal.

Comment

A composition in accordance with the present invention has advantages over any foreshadowed in the aforementioned U.S. Pat. No. 3,839,557 in that it allows delivery of the antibiotic to young suckling ruminants as part of their milk diet by incorporation in the milk replacer powder during manufacture or at mixing of the milk replacer with water. This is more practical than dosing with a tablet, drenching or adding to water and over any disclosed in EP 0139595 in that no organic solvent for the ionophore antibiotic is a prerequisite. EP 0139595 discloses no example of a composition not requiring an organic solvent.

An omission of an organic solvent as a precursor to suspension in water of the antibiotic has several advantages Monensin has poor solubility in all organic solvents except methyl alcohol (a poison to mammals) and n-propyl alcohol—when these solutions are added to water monensin crystallises out of solution other features

- non flammable
- no odour
- no separation problems (as above)
- cost effective
- simple manufacturing process
- high concentration of active monensin
- easily mixed with powders, water and can be sprayed
- better stability in a powder form.

What is claimed is:

1. A calf feed composition comprising a substantially homogeneous aqueous suspension of, when expressed by weight per liter of solution:

1) from 2 mg–16 mg of a composition comprising
   a) from 90 to 95% of crystalline monensin;
   b) from 0.1 to 2% of an antifoam agent comprising silicone powder;
   c) from 0.1 to 5% of a wetting agent comprising sodium lauryl sulfate;
   d) from 0.1 to 5% of a dispersal agent comprising colloidal anhydrous silica; and
   e) from 0.1 to 5% of a suspension agent comprising a galactomannan;
   said amounts expressed by weight with respect to the total weight of 1(a) through 1(e); and
2) from 5 g–30 g of a milk replacer composition; or
3) from 1 g–3 g of a milk extender composition; or
4) from 5 g–30 g of a milk replacer composition and from 1 g–3 g of a milk extender composition;

in the absence of an organic solvent.

2. The calf feed composition of claim 1 wherein said galactomannan is guar gum.

3. A calf feed composition comprising a substantially homogeneous aqueous suspension of, when expressed by weight per liter of solution:

a) from 2 to 16 mg/L of a composition comprising
   95% when expressed as the sodium salt of crystalline sodium monensin,
   1.9% silicone antifoam powder,
   3.5% sodium lauryl sulfate,
   2.5% colloidal anhydrous silica, and
   1.5% Guar gum, said amounts expressed by weight with respect to the total weight of a, and
b) 15 to 20 g/L of a milk replacer composition, or 1 to 3 g/L of a milk extender composition, or 15 to 20 g/L of a milk replacer composition and 1 to 3 g/L of a milk extender composition;

in the absence of an organic solvent.

* * * * *